US00PP25920P3

(12) United States Plant Patent
Miller

(10) Patent No.: US PP25,920 P3
(45) Date of Patent: Sep. 22, 2015

(54) ***LANTANA* PLANT NAMED 'LORD BROOKS'**

(50) Latin Name: *Lantana montevidensis*
Varietal Denomination: Lord Brooks

(71) Applicant: Luen Miller, Santa Cruz, CA (US)

(72) Inventor: Luen Miller, Santa Cruz, CA (US)

( * ) Notice: Subject to any disclaimer, the term of this patent is extended or adjusted under 35 U.S.C. 154(b) by 55 days.

(21) Appl. No.: 13/999,020

(22) Filed: Dec. 31, 2013

(65) Prior Publication Data

US 2015/0189808 P1 Jul. 2, 2015

(51) Int. Cl.
*A01H 5/00* (2006.01)

(52) U.S. Cl.
USPC ..... Plt./227

(58) Field of Classification Search
USPC ..... Plt./227
CPC ..... A01H 5/02; A01H 5/00
See application file for complete search history.

*Primary Examiner* — Kent L Bell
(74) *Attorney, Agent, or Firm* — Cassandra Bright

(57) ABSTRACT

A new and distinct *Lantana* cultivar named 'LORD BROOKS' is disclosed, characterized by distinctive dark lavender flowers and a low growing, trailing habit. The new variety is a *Lantana,* normally produced as an outdoor garden or container plant.

1 Drawing Sheet

Latin name of the genus and species: *Lantana montevidensis.*

Variety denomination: 'LORD BROOKS'.

BACKGROUND OF THE INVENTION

The new *Lantana* cultivar is a product of a chance discovery by the inventor, Luen Miller. The new variety was discovered as a naturally occurring single branch mutation of an unnamed, unpatented variety of *Lantana montevidensis.*

Mr. Miller discovered the new variety in a commercial planting of the parent variety at his nursery in Royal Oaks, Calif. during the February of 1999.

Asexual reproduction of the new cultivar 'LORD BROOKS' by vegetative cuttings was first performed at a commercial nursery in Aug. 17, 1999. Subsequently, several generations have been produced, and have shown that the unique features of this cultivar are stable and reproduced true to type in successive generations. During this evaluation period, plants were kept in confidential locations at the inventor's nursery, not accessible to the public.

SUMMARY OF THE INVENTION

The cultivar 'LORD BROOKS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LORD BROOKS' These characteristics in combination distinguish 'LORD BROOKS' as a new and distinct *Lantana* cultivar:

1. Dark lavender flower color
2. Outwardly spreading plant habit
3. Low growing plant habit.
4. Lack of seed production.

PARENT COMPARISON

Plants of the new cultivar 'LORD BROOKS' are comparable to the parent *Lantana montevidensis* unpatented. The two *Lantana* varieties are similar in most horticultural characteristics however, the new variety 'LORD BROOKS' differs in having darker colored flowers.

COMMERCIAL COMPARISON

Plants of the new cultivar 'LORD BROOKS' are comparable to the variety *Lantana montevidensis* 'Lady Brooks', filed concurrently U.S. Plant patent application Ser. No. 13/999,019. The two *Lantana* varieties are similar in most horticultural characteristics however, the new variety 'LORD BROOKS' differs in having darker colored flowers.

Plants of the new cultivar 'LORD BROOKS' are comparable to the commercial variety *Lantana sellowiana* 'Monswee' U.S. Plant Pat. No. 7,626. The two *Lantana* varieties are similar in most horticultural characteristics, including the characteristic trailing plant habit. Plants of the new variety 'LORD BROOKS', however, have dark lavender flowers, whereas flowers of 'Monswee' are both lavender and white on the same plant.

BRIEF DESCRIPTION OF THE PHOTOGRAPH

FIG. 1: Illustrates in full color a closeup view of flowers of 'Lord Brooks', together with its closest comparator, and with the parent variety:

Flowers of 'LORD BROOKS' are the darkest colored flowers in the center.

Flowers of 'LADY BROOKS' are the lightest colored flowers on the left side of the grouping.

Flowers of the parent variety *Lantana montevidensis* are on the right side of the grouping, with medium lavender colored flowers.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'LORD BROOKS' plants grown approximately 30 weeks outdoors in Royal Oaks, Calif. The growing temperature ranged from 10° C. to 20° C. during the night and from 15° C. to 35° C. during the day. General light conditions are bright, normal sunlight. Measurements and numerical values represent averages of typical plant types.

Botanical classification: *Lantana montevidensis* 'LORD BROOKS'.

PROPAGATION

Time to initiate roots: 6 to 8 days at approximately 15° C.
Root description: Fibrous.

PLANT

Growth habit: Flat and spreading.
Pot size of plant described: 1 gallon.
Height: 14 cm.
Plant spread: 48 cm.
Growth rate: Rapid.
Branching characteristics: Freely Branches at each internode with two lateral branches.
Length of primary lateral branches: Average 38 cm.
Diameter of lateral branches: 0.3 cm.
Quantity of primary lateral branches: 12
Characteristics of primary lateral branches:
- *Form*.—Round.
- *Diameter*.—0.25 cm.
- *Color*.—Near RHS Greyed-Green 197A.
- *Texture*.—Pubescent, becoming scaly with age.
- *Strength*.—Soft and very flexible when young, woody and slightly brittle with age.

Internode length: 2 to 4 cm.

FOLIAGE

Leaf:
- *Arrangement*.—Opposite.
- *Quantity*.—Approximately 16-20 per branch.
- *Average length*.—4.0 cm.
- *Average width*.—2.0 cm.
- *Shape of blade*.—Ovate.
- *Apex*.—Acute.
- *Base*.—Attenuate to cordate.
- *Margin*.—Crenate.
- *Texture of top surface*.—Pubescent.
- *Texture of lower surface*.—Pubescent.
- *Aspect*.—Flat.
- *Color*.—Young foliage upper side: Near RHS Green 137A. Young foliage under side: Near RHS Green 138B. Mature foliage upper side: Near RHS Green 137A. Mature foliage under side: Near RHS Green 138A.
- *Venation*.—Type: Pinnate. Venation color upper side: Near RHS Yellow-Green 144B. Venation color under side: Near RHS Green 137A.
- *Petiole*.—Length: 0.6 cm. Diameter: 0.1 cm. Color: Near RHS Yellow-Green 144B. Texture: Slightly Pubescent.

FLOWER

Natural flowering season: Continuous Flowers in Warm Climate.
Days to flowering from rooted cutting: Approximately 28.
Inflorescence and flower type and habit: Corymb.
Rate of flower opening: 4 to 5 days from bud to fully opened flower.
Flower longevity on plant: 8-10 days.
Persistent or self-cleaning: Self cleaning.
Overall inflorescence size:
- *Height*.—Approximately 2.0 cm.
- *Diameter*.—Approximately 3.1 cm.

Individual flower size:
- *Length*.—Approximately 1.4 cm including corolla tube.
- *Diameter*.—Approximately 0.8 cm.

Bud:
- *Shape*.—Squared tubular.
- *Length*.—1.0 cm including corolla tube.
- *Diameter*.—0.3 cm.
- *Color*.—Near RHS Purple N79C.

Corolla:
- *Petals/lobes*.—Number: 4. Length: 0.5 cm. Width: 0.5. Shape: Salverform. Aspect: Slightly cupped with a long slender tube. Margin: Entire. Texture: Glabrous. Color: When opening: Upper surface: Near RHS Purple N79B. Lower surface: Near RHS Purple N79D. Fully opened: Upper surface: Near RHS Purple N79C. Lower surface: Near RHS Purple N79C.
- *Throat/tube*.—Color: Interior: Near RHS Red-Purple 71B. Exterior Near Red-Purple 72B. Texture: Smooth.

Calyx/sepals:
- *Form*.—5 Fused sepals.
- *Length*.—0.3 cm.
- *Diameter*.—0.1 cm.
- *Sepal shape*.—5 Fused sepals form a tube.
- *Sepal margin*.—Fused.
- *Sepal texture*.—Smooth.
- *Sepal color*.—Upper surface: Green 137B. Lower surface: Green 137B.

Flower bracts/inflorescence bracts:
- *Appearance*.—Matte.
- *Length*.—Approximately 0.9 cm.
- *Width*.—Approximately 0.1 cm.
- *Shape*.—Narrow deltoid.
- *Aspect*.—Cupped.
- *Apex*.—Acute.
- *Margin*.—Entire.
- *Texture*.—All surfaces glabrous.
- *Color*.—Near RHS 137A all surfaces.

Peduncles:
- *Length*.—Average 3.2 cm.
- *Diameter*.—Approximately 0.1 cm.
- *Angle*.—About 25 degrees.
- *Strength*.—Strong, flexible.
- *Texture*.—Pubescent.
- *Color*.—Yellow-Green 144A.
- *Flower fragrance*.—Mild.

REPRODUCTIVE ORGANS

Stamens:

*Number* (*per flower*).—4.

*Filament length.*—0.1 cm.

*Anthers*.—Shape: Ovate. Length: 0.1 cm. Color: Near RHS N77A.

Pollen: Not observed.

Pistils:

*Quantity per flower.*—1, total length 0.25 cm, all parts compressed and indistinguishable.

OTHER CHARACTERISTICS

Seed: Not observed.

Disease/pest resistance: Neither resistance nor susceptibility to pathogens and pests common to *Lantana* have been observed.

Temperature tolerance: The new variety tolerates temperatures between 0 to 40° C.

What is claimed is:

1. A new and distinct cultivar of *Lantana* plant named 'LORD BROOKS' as herein illustrated and described.

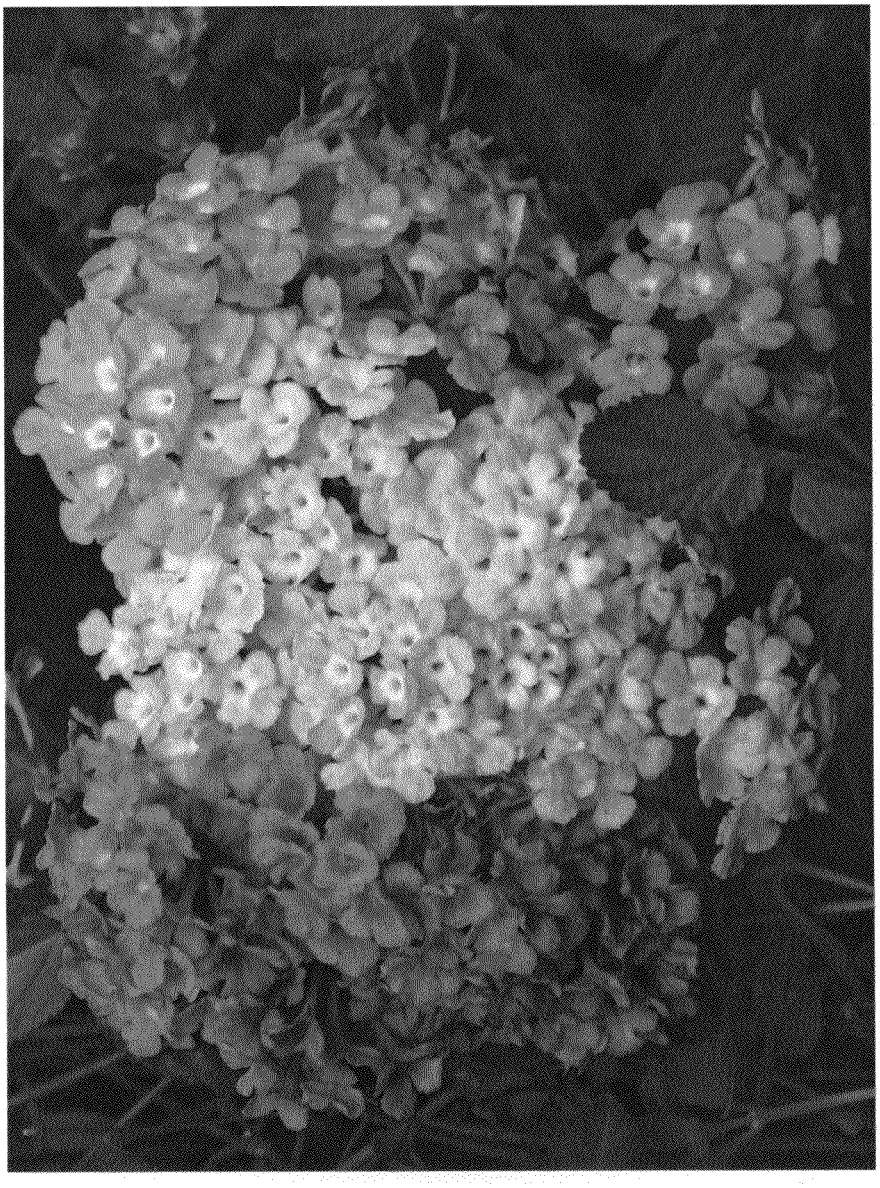

* * * * *